United States Patent [19]

Neumann et al.

[11] Patent Number: 4,990,660

[45] Date of Patent: Feb. 5, 1991

[54] PREPARATION OF AROMATIC HYDROXYCARBOXYLIC ACIDS

[75] Inventors: Peter Neumann, Mannheim; Ulrich Eichenauer, Frankfurt, both of Fed. Rep. of Germany

[73] Assignee: BASF Aktiengesellschaft, Ludwigshafen, Fed. Rep. of Germany

[21] Appl. No.: 287,034

[22] Filed: Dec. 21, 1988

[30] Foreign Application Priority Data

Dec. 22, 1987 [DE] Fed. Rep. of Germany ....... 3743517

[51] Int. Cl.$^5$ ............................................ C07C 315/00
[52] U.S. Cl. .................................... 562/427; 560/130; 560/131; 562/421; 562/429; 562/432; 562/434; 562/435; 562/467; 562/469; 562/474; 562/475; 562/476
[58] Field of Search .............. 562/421, 429, 432, 467, 562/469, 475, 473, 474, 476, 434, 435; 560/131, 130

[56] References Cited

U.S. PATENT DOCUMENTS 4,665,215 5/1987 Daenport .................... 560/130
4,692,546 9/1987 Davenport .................... 560/130

FOREIGN PATENT DOCUMENTS 170483 2/1986 European Pat. Off. .
0216279 4/1987 European Pat. Off. .

OTHER PUBLICATIONS

Houben-Weyl, Methoden der Organischen Chemie, vol. 7/3b, pp. 15–17.
Tetrahedron 32 (1976), p. 1835.
Organic Reactions 1 (1942), p. 342.

*Primary Examiner*—Michael L. Shippen
*Attorney, Agent, or Firm*—Oblon, Spivak, McClelland, Maier & Neustadt

[57] ABSTRACT

Aromatic hydroxycarboxylic acids of the formula $$(HO-)_n A-COOH$$

where n is 1 or 2 and A is a radical from the benzene, naphthalene, biphenyl, diphenyl ether, diphenyl sulfide or diphenyl sulfone series, are prepared by a process in which an acylated aromatic compound of the formula $$(R^1-CO-O-)_n A-CO-R^2$$

where $R^1$ and $R^2$ independently of one another are each unsubstituted or substituted $C_1$–$C_4$-alkyl and n and A each have the abovementioned meanings, is oxidized with oxygen in the presence of a catalyst and of a solvent at from 20° to 250° C. to give a carboxylic acid of the formula $$(R^1-CO-O-)_n A-COOH$$

where $R^1$, n and A have the abovementioned meanings, and the acyl group or groups is or are then eliminated.

10 Claims, No Drawings

PREPARATION OF AROMATIC HYDROXYCARBOXYLIC ACIDS

The present invention relates to a novel process for the preparation of aromatic hydroxycarboxylic acids by oxidizing the corresponding ketones, in which the hydroxyl groups are acylated, by means of oxygen in the presence of a catalyst and of a solvent to give an aromatic hydroxycarboxylic acid in which the hydroxyl groups are acylated, and then eliminating the acyl groups.

It is known that simple aromatic hydroxycarboxylic acids can be prepared by the Kolbe reaction, i.e. carboxylation of the corresponding phenolates with carbon dioxide.

It is also known that aromatic carboxylic acids can be obtained from acetophenones by the haloform reaction, i.e. reaction with a halogen in an alkaline medium. This process, which is frequently carried out using sodium hypochlorite, results in a number of side reactions in the case of aromatics which are substituted by electron-donating groups. For example, protective groups which can be hydrolyzed in an alkaline medium can be eliminated, or halogenation of the nucleus or oxidation of the nucleus may occur.

It is an object of the present invention to provide a novel process which permits the preparation of aromatic hydroxycarboxylic acids in an advantageous manner, the formation of byproducts being avoided as far as possible.

We have found that this object is achieved and that aromatic hydroxycarboxylic acids of the formula I

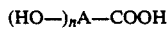
$$(HO{-})_n A{-}COOH \qquad (I)$$

where n is 1 or 2 and A is a radical from the benzene, naphthalene, biphenyl, diphenyl ether, diphenyl sulfide or diphenyl sulfone series, can be advantageously prepared if an acylated aromatic compound of the formula II

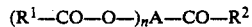
$$(R^1{-}CO{-}O{-})_n A{-}CO{-}R^2 \qquad (II)$$

where $R^1$ and $R^2$ are identical or different and independently of one another are each unsubstituted or substituted $C_1$–$C_4$-alkyl and n and A each have the abovementioned meanings, is oxidized with oxygen in the presence of a catalyst and of a solvent at from 20° to 250° C. to give a carboxylic acid of the formula III

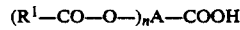
$$(R^1{-}CO{-}O{-})_n A{-}COOH \qquad (III)$$

where $R^1$, n and A have the abovementioned meanings, and the acyl group or groups is or are then eliminated.

EP-A-No. 216 279 has disclosed a process in which 5-chlorothiophene-2-carboxylic acid and 3-chlorothiophene-2-carboxylic acid are prepared by oxidizing the corresponding 2-acetyl compounds with oxygen in the presence of manganese acetate or cobalt acetate as a catalyst in glacial acetic acid.

In the oxidation of the acylated aromatic compound II under the stated conditions, it was to be expected that, just as the acyl group $-CO-R^2$ is oxidized to the carboxyl group, the acyloxy group $-O-CO-R^1$ too would be oxidized, resulting in products having free phenolic OH groups, which are known to undergo a further oxidative reaction, the aromatic ring usually being oxidized (see Houben-Weyl, Methoden der organischen Chemie, Volume 7/3b, pages 15-17).

It was therefore surprising that, under the conditions of the novel process, the acyloxy group $-O-CO-R^1$ does not undergo oxidative decomposition. Furthermore, it could not be foreseen that there would be no formation of byproducts in which, regardless of the acyloxy group, oxidation of the aromatic nucleus occurs.

The aromatic radical A in formula I is derived from benzene, naphthalene, biphenyl, diphenyl ether, diphenyl sulfide or diphenyl sulfone, each of which is unsubstituted or substituted.

Examples of suitable substituents are halogen, such as fluorine, chlorine or bromine, nitro, carboxyl or hydroxysulfonyl.

If n is 1, examples of suitable divalent radicals —A— are

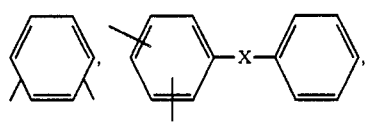

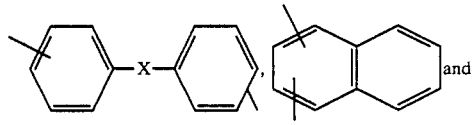

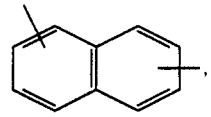

where X is a chemical bond, O, S or $SO_2$ and, as stated above, the aromatic nuclei may be further substituted.

Corresponding trivalent molecular fragments are obtained if n is 2, and in this case too the aromatic system may be further substituted, and in polynuclear systems acylated hydroxyl groups may furthermore be bonded to different aromatic nuclei.

$R^1$ and $R^2$ are each, for example, methyl, ethyl, propyl, isopropyl, butyl, isobutyl or tert-butyl.

If $R^1$ and/or $R^2$ are substituted, suitable substituents are, for example, halogen, in particular chlorine, $C_1$–$C_4$-alkoxy, such as methoxy, ethoxy, propoxy or butoxy, and $C_1$–$C_4$-alkanoyloxy, such as formyloxy, acetyloxy, propionyloxy or butyryloxy.

Radicals $R^1$ and $R^2$ substituted in this manner are, in particular, chloromethyl, methoxymethyl, ethoxymethyl, formyloxymethyl, acetyloxymethyl or propionyloxymethyl.

Preferably oxidized acylated aromatic compounds of the formula II are those in which $R^1$ and $R^2$ independently of one another are each methyl or ethyl.

Other acylated aromatic compounds of the formula II which are preferably oxidized are those in which A is

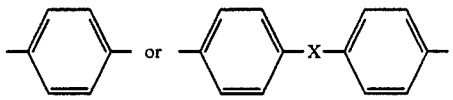

where X is a chemical bond or oxygen.

Suitable solvents are all organic solvents which are inert under the conditions of the novel process, $C_1$-$C_5$-carboxylic acids being preferably used Examples are formic acid, acetic acid, propionic acid, butyric acid, valeric acid and pivalic acid. Propionic acid is a particularly preferably used solvent.

Examples of catalysts used are metal salts, in particular the salts of vanadium, manganese, iron or cobalt. Examples of suitable anions are phosphate, sulfate, halide, such as fluoride, chloride or bromide, and carboxylates, such as formate, acetate, propionate or butyrate. The particular sulfates, halides or acetates are preferably used. Those of the stated metal acetates in which the oxidation state of the particular metal is +2 are very particularly noteworthy.

In a preferred embodiment, mixtures of the stated metal salts are used as catalysts, and cobalt salts and manganese salts may be mentioned in particular as components of this mixture.

The amount of the catalyst to be used can be varied in a wide range. The catalysts are particularly advantageously used in an amount of from $5 \times 10^{-3}$ to $5 \times 10^{-1}$ mole of metal salt per mole of compound II.

In a preferred procedure, the oxidation is carried out in the presence of a carboxylic anhydride of 3 to 8 carbon atoms.

As a rule, the carboxylic anhydride is added in an amount of from 0.5 to 3, preferably from 1 to 2, moles per mole of the acylated aromatic compound II.

Examples of suitable carboxylic anhydrides are acetic anhydride, propionic anhydride and the mixed anhydrides of formic acid and acetic acid, formic acid and propionic acid or acetic acid and propionic acid.

The reaction temperature is from 20° to 250° C., preferably from 90° C. to the boiling point of the reaction mixture. The reaction is carried out, as a rule, under from 0.9 to 200, preferably 1, bar.

According to the invention, the oxidizing agent used is oxygen. The oxygen may be used in pure form or as a mixture with inert gas, for example nitrogen. A preferably used oxidizing agent is air. Gassing is advantageously effected via a valve in the base.

The novel process, which may be operated continuously or batchwise, is advantageously carried out by initially taking the acylated aromatic compound II, if required the carboxylic anhydride, the solvent and the catalyst in a suitable reactor, for example a flanged reactor, and heating the stirred mixture to the temperature according to the invention, oxygen simultaneously being passed through the reaction mixture. After the reaction time of, in general, from 2 to 10 hours, the oxidation is complete, and the reaction mixture is cooled and then filtered, and the filter residue washed with water and dried. It is also possible first to add the reaction mixture to water and then to carry out the filtration.

The filter residue thus treated essentially consists of the acylated hydroxycarboxylic acid III, in which the acyl group or groups is or are then eliminated by a conventional method. For this purpose, the compound III can be heated together with potassium hydroxide or sodium hydroxide in water or treated with a dilute mineral acid, eg. dilute hydrochloric acid or dilute sulfuric acid, at elevated temperatures. However, the O-acyl group can also be eliminated by transesterification, for example with methanol or ethanol.

The acylated aromatic compounds of the formula II are readily obtainable by processes described in the literature. For example, phenols can be converted into the appropriately C-, O-diacylated derivatives in a Friedel-Crafts acylation reaction (see, for example, the conversion of 4-hydroxybiphenyl into 1-acetoxy-4'-acetylbiphenyl—Tetrahedron 32 (1976), 1835). Another possible synthesis is, for example, the Fries rearrangement (see Org. Reactions 1 (1942), 342), i.e. the rearrangement of acylated phenols to give hydroxyacetophenones, with subsequent O-acylation by standard methods.

The aromatic hydroxycarboxylic acids of the formula I which are obtained by the novel process are, for example, useful monomers for the preparation of thermotropic liquid-crystalline polymers.

The Examples which follow illustrate the invention.

EXAMPLE 1

500 ml of glacial acetic acid, 50.8 g of 4-acetoxy-4'-acetylbiphenyl, 0.8 g of cobalt(II) acetate and 12.0 g of manganese(II) acetate were refluxed in a 1 l double-walled flanged reactor equipped with an intensive stirrer and baffles, and the mixture was gassed with air via a valve in the base. After 4 hours, the mixture was cooled and the product was filtered off under suction, washed with water and dried. 26.1 g (51% yield) of 4-acetoxybiphenyl-4'-carboxylic acid having a purity of >98% (HPLC) were obtained.

EXAMPLE 2

500 ml of propionic acid, 50.8 g of 4-acetoxy-4'-acetyldiphenyl, 0.8 g of cobalt(II) acetate and 12.0 g of manganese(II) acetate were refluxed in a 1 l double-walled flanged reactor equipped with an intensive stirrer and baffles, and the mixture was gassed with air via a valve in the base. After 4 hours, the mixture was cooled and the product was filtered off under suction, washed with water and dried. 37.9 g (74% yield) of 4-acetoxybiphenyl-4'-carboxylic acid having a purity of >98% (HPLC) were obtained.

EXAMPLE 3

25 g of 4-acetoxybiphenyl-4'-carboxylic acid in 100 ml of 5% strength by weight sodium hydroxide solution were heated at 80° C. for 1 hour. The hot reaction mixture was acidified with concentrated hydrochloric acid and the residue was filtered off, washed with water and dried. 20.6 g (98% yield) of 4-hydroxydiphenyl-4'-carboxylic acid having a purity of >99% (HPLC) were obtained.

EXAMPLE 4

345 g of 4-acetoxy-4'-acetylbiphenyl were suspended in 2.6 l of propionic acid. 2.6 g of cobalt(II) acetate, 10.1 g of manganese(II) acetate and 375 g of acetic anhydride were added to this suspension, and the mixture was heated to 110° C. The mixture was stirred for 15 minutes at 110° C., after which it was gassed with air via a valve in the base. After gassing had been carried out for 90 minutes at 110° C., the reaction was complete; the reaction mixture was discharged through the valve in the base, and the product was filtered off under suction and washed with petroleum ether. 291.3 g (84% yield) of acetoxybiphenylcarboxylic acid having a purity of 99.9% (HPLC) were obtained.

The acylated aromatic compounds II stated in the Table are converted into the hydroxycarboxylic acids I in a similar manner.

TABLE

| Example No. | II | I |
|---|---|---|
| 5 | CH₃O—OC—⟨C₆H₄⟩—COCH₃ | HO—⟨C₆H₄⟩—COOH |
| 6 | CH₃O—OC—⟨C₆H₃⟩(—CO—OCH₃)—COCH₃ | HO—⟨C₆H₃⟩(—OH)—COOH |
| 7 | CH₃O—OC—⟨C₆H₄⟩—O—⟨C₆H₄⟩—COCH₃ | HO—⟨C₆H₄⟩—O—⟨C₆H₄⟩—COOH |
| 8 | CH₃O—OC, CH₃OC — naphthalene | HO, HOOC — naphthalene |
| 9 | CH₃O—OC — naphthalene — COCH₃ | HO — naphthalene — COOH |
| 10 | CH₃O—OC — naphthalene — COCH₃ | HO — naphthalene — COOH |

We claim:

1. A process for the preparation of an aromatic hydroxycarboxylic acid of the formula (I):

$$(HO—)_n A—COOH \quad (I)$$

wherein n is 1 or 2, and A is a radical selected from the group consisting of naphthalene, biphenyl, diphenyl ether, diphenyl sulfide and diphenyl sulfone and said radicals substituted by halogen, nitro, carboxyl and hydroxylsulfonyl, which comprises oxidizing:

(a) an acylated aromatic compound of the formula (II):

$$(R^1—CO—O—)_n A—CO—R^2 \quad (II)$$

wherein $R^1$ and $R^2$ are identical or different and independently of one another are each $C_1$-$C_4$-alkyl or $C_1$-$C_4$-alkyl substituted with halogen, $C_1$-$C_4$-alkoxy or $C_1$-$C_4$-alkanoyloxy; with substantially pure oxygen or a mixture of oxygen and an inert gas in the presence an effective amount of a salt of vanadium, manganese, iron or cobalt as a catalyst and propionic acid as a solvent at a temperature of from about 20° C. to 250° C., to form a carboxylic acid of the formula (III):

$$(R^1—CO—O—)_n A—COOH \quad (III)$$

wherein $R^1$, n and A are as defined above, and then (b) subjecting the acyl group or groups to either hydrolysis or transesterification to eliminate the acyl group or groups to form said aromatic hydroxy carboxylic acid.

2. The process as claimed in claim 1, wherein said oxidation is carried out in the presence of a carboxylic anhydride of 3 to 8 carbon atoms.

3. The process as claimed in claim 1, wherein $R^1$ and $R^2$ are each methyl, ethyl, propyl, isopropyl, butyl, isobutyl, tert-butyl, chloromethyl, methoxymethyl, ethoxymethyl, formyloxymethyl, acetyloxymethyl or propionyloxymethyl.

4. The process as claimed in claim 1, wherein $R^1$ and $R^2$ are each methyl or ethyl.

5. The process as claimed in claim 1, wherein said salts of vanadium, manganese, iron or cobalt are phosphates, sulfates, halides or carboxylates.

6. The process as claimed in claim 5, wherein said salts are sulfates, halides or acetates.

7. The process as claimed in claim 1, wherein from $5 \times 10^{-3}$ to $5 \times 10^{-1}$ mole of metal salt per mole of the aromatic compound of the formula (II) is used.

8. The process as claimed in claim 2, wherein said carboxylic anhydride is added in an amount of from 0.5 to 3 moles per mole of the acylated aromatic compound of the formula (II).

9. The process as claimed in claim 1, wherein said hydrolysis is effected by aqueous potassium hydroxide or sodium hydroxide or dilute aqueous hydrochloric acid or sulfuric acid.

10. The process as claimed in claim 1, wherein said transesterification is effected by methanol or ethanol.

* * * * *